(12) United States Patent
Shrivastav

(10) Patent No.: US 9,341,512 B2
(45) Date of Patent: May 17, 2016

(54) FREQUENCY RESPONSE OF VIBRATION SENSORS

(71) Applicant: Prabhat Shrivastav, Mysore (IN)

(72) Inventor: Prabhat Shrivastav, Mysore (IN)

(73) Assignee: Fluke Corporation, Everett, WA (US)

(*) Notice: Subject to any disclaimer, the term of this patent is extended or adjusted under 35 U.S.C. 154(b) by 290 days.

(21) Appl. No.: 13/840,307

(22) Filed: Mar. 15, 2013

(65) Prior Publication Data

US 2014/0260641 A1 Sep. 18, 2014

(30) Foreign Application Priority Data

Mar. 15, 2013 (IN) .............................. 302/KOL/2013

(51) Int. Cl.
| | |
|---|---|
| *G01N 29/26* | (2006.01) |
| *G01N 29/14* | (2006.01) |
| *G01H 11/06* | (2006.01) |
| *G01D 3/032* | (2006.01) |
| *G01H 1/00* | (2006.01) |

(52) U.S. Cl.
CPC .............. *G01H 11/06* (2013.01); *G01D 3/032* (2013.01); *G01H 1/00* (2013.01); *G01N 29/26* (2013.01)

(58) Field of Classification Search
CPC ..... G01N 29/14; G01N 29/045; G01N 29/12; G01N 29/42; G01N 29/2437; G01N 29/227; G01N 29/36; G01N 29/48; G01N 29/46; G01N 29/041; G01H 1/00; G01H 1/12; G01H 11/06; G01H 11/04; G01D 3/032
USPC ............ 73/658, 660, 587, 579, 593, 584, 649
See application file for complete search history.

(56) References Cited

U.S. PATENT DOCUMENTS

| | | | | |
|---|---|---|---|---|
| 4,520,674 A | * | 6/1985 | Canada et al. ................... | 73/660 |
| 4,724,524 A | * | 2/1988 | Thomas ............. | G05B 19/4065 340/680 |
| 4,806,914 A | * | 2/1989 | Thomas ................... | G01H 1/16 340/680 |
| 4,853,680 A | * | 8/1989 | Thomas ........................ | 340/680 |
| 5,069,071 A | * | 12/1991 | McBrien ................ | G01H 11/06 73/579 |
| 5,633,811 A | | 5/1997 | Canada et al. | |
| 5,646,350 A | * | 7/1997 | Robinson ............ | G01M 13/028 73/599 |
| 6,053,047 A | * | 4/2000 | Dister et al. .................... | 73/593 |
| 6,065,332 A | * | 5/2000 | Dominick ................ | G01H 1/10 175/56 |
| 6,209,400 B1 | * | 4/2001 | Schoch et al. ................... | 73/778 |
| 6,275,781 B1 | * | 8/2001 | Maness ............... | G01M 13/045 702/182 |
| 6,408,679 B1 | * | 6/2002 | Kline-Schoder et al. .... | 73/19.03 |

(Continued)

FOREIGN PATENT DOCUMENTS

EP  0 006 315 A1  1/1980

OTHER PUBLICATIONS

Extended EP Search Report for EP 14159290.7, mailing date Feb. 3, 2015, 7 pages.

*Primary Examiner* — Helen Kwok

(74) *Attorney, Agent, or Firm* — Seed IP Law Group PLLC

(57) ABSTRACT

Frequency compensation of a vibration sensor digitally in a time domain by using a high-pass filter roll-off slope is presented. The subject matter reduces the noise floor of an analog front end or analog domain portion of a circuit configured to enhance the frequency response of a vibration sensor. The present subject matter eliminates or reduces analog components and adds pieces of signal processing software to digitally enhance the frequency response of a vibration sensor so as to reduce component costs.

20 Claims, 8 Drawing Sheets

(56) References Cited

U.S. PATENT DOCUMENTS

| | | | |
|---|---|---|---|
| 6,725,705 B1* | 4/2004 | Huebler et al. | 73/40.5 A |
| 7,860,663 B2* | 12/2010 | Miyasaka et al. | 702/35 |
| 8,781,762 B2* | 7/2014 | Macleod et al. | 702/56 |
| 2002/0043106 A1* | 4/2002 | Board | 73/579 |
| 2003/0164761 A1 | 9/2003 | Levinzon | |
| 2004/0211260 A1* | 10/2004 | Girmonsky | A61B 5/0215 73/579 |
| 2008/0082296 A1 | 4/2008 | Robinson et al. | |
| 2009/0249880 A1* | 10/2009 | Lim | G01M 7/025 73/659 |
| 2011/0301872 A1* | 12/2011 | Hedin | 702/34 |
| 2013/0130734 A1* | 5/2013 | Rice | G01M 5/0066 455/517 |

\* cited by examiner

FREQUENCY RESPONSE OF VIBRATION SENSORS

TECHNICAL FIELD

The present subject matter is generally related to analog-digital signal processing, and more particularly, it relates to digitally enhancing frequency response of vibration sensors.

BACKGROUND

Mechanical machinery of every kind is used in every aspect of our daily lives, from electric toothbrushes and washer/dryers people use at home to industrial machines used by companies to manufacture nearly every conceivable product. When a machine fails or breaks down, the consequences can range from irritation to financial misfortune or from personal injury to possible loss of life. For this reason, early detection, identification, and correction of machinery problems is of supreme importance. One method that facilitates such early detection and identification involves sensing a vibration signal generated by machinery vibration so as to detect not only when a machine is developing a problem, but to identify the specific nature of the problem for correction. Because the detected vibration signal is analog in nature, an analog circuit that is configured to capture the frequency response of the vibration signal is very complex. Such complexity limits signal range for analysis, however, and worse, requires costly components to manufacture a vibration meter in which the vibration sensor is housed.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

One aspect of the present subject matter includes a system form reciting a vibration meter, comprising an analog-to-digital converter configured to convert an attenuated vibration signal to a converted signal. The vibration meter further comprises a digital frequency enhancement block on which hardware runs various pieces of signal processing software configured to enhance frequency response of the converted signal. The converted signal is amplified by amplifying time domain samples of the attenuated vibration signal to produce an amplified signal. The amplified signal is filtered to produce a filtered signal by a digital high pass filter with a calculated roll-off slope based on an initial frequency of a frequency band within which the frequency response of the converted signal remains somewhat uniform.

Another aspect of the present subject matter includes a method form reciting a method comprising converting an attenuated vibration signal by an analog-to-digital converter to a converted signal. The method further comprises digitally enhancing frequency response of the converted signal by a digital frequency enhancement block. The converted signal is amplified by amplifying time domain samples of the attenuated vibration signal to produce an amplified signal. The amplified signal is filtered to produce a filtered signal by a digital high pass filter with a calculated roll-off slope based on an amplitude at an initial frequency of a frequency band within which the frequency response of the converted signal remains somewhat uniform.

A further aspect of the present subject matter includes a computer-readable medium form reciting a tangible computer-readable medium on which computer-executable instructions are stored to implement a method comprising converting an attenuated vibration signal by an analog-to-digital converter to a converted signal. The method further comprises digitally enhancing frequency response of the converted signal by a digital frequency enhancement block. The converted signal is amplified by amplifying time domain samples of the attenuated vibration signal to produce an amplified signal. The amplified signal is filtered to produce a filtered signal by a digital high pass filter with a calculated roll-off slope based on an amplitude at an initial frequency of a frequency band within which the frequency response of the converted signal remains somewhat uniform.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Various embodiments of the present subject matter are directed to frequency compensation of a vibration sensor digitally in a time domain by using a high-pass filter roll-off slope. A few embodiments of the present subject matter reduce the noise floor of an analog front end or analog domain portion of a circuit configured to enhance the frequency response of a vibration sensor. Several embodiments of the present subject matter eliminate or reduce analog components and add pieces of signal processing software to digitally enhance the frequency response of a vibration sensor so as to reduce component costs. In all embodiments, a vibration meter incorporating the subject matter of the embodiments is configured to measure about 0.1 G of vibration acceleration or about 10 mV in vibration amplitude (or about −60 dB in vibration amplitude). In a few embodiments, a vibration meter incorporating the subject matter of the few embodiments is configured to measure up to about 0.003 G of vibration acceleration or about 0.3 mV in vibration amplitude. In all embodiments, the subject matter lacks analog frequency compensation components. In various embodiments, the subject matter has a noise floor close to or better than −120 dB by selectively controlling the number of bits in an analog-to-digital converter in the digital domain portion of the circuit configured to enhance the frequency response of the vibration sensor.

Figure 1A:
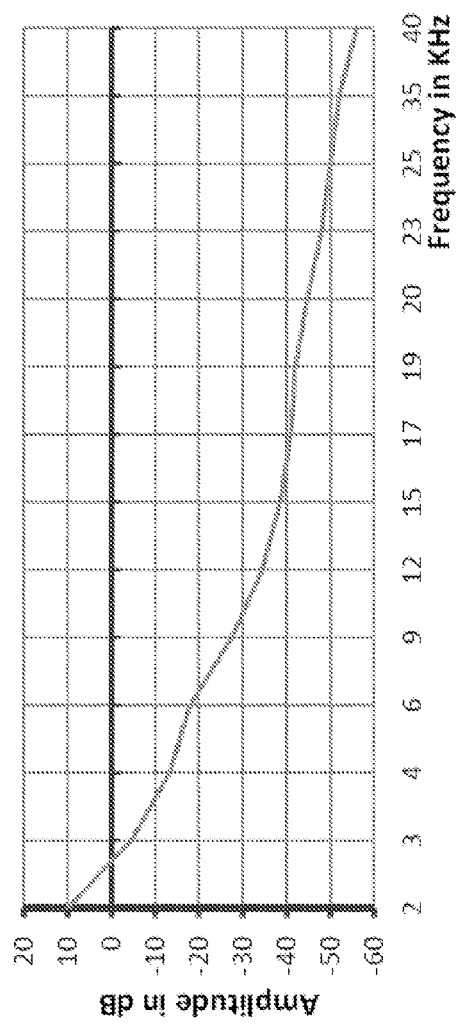
FIG. 1A illustrates an archetypical vibration meter for vibration screening of a mechanical workpiece.

FIG. 1A illustrates a system 100 in which a maintenance person uses a vibration meter to monitor vibration of a machine workpiece. The vibration meter allows the maintenance person to screen for mechanical issues, allows reliable and repeatable measurements of the machine workpiece to facilitate maintenance decisions, permits the ability to read vibration trends over time and notify others when something abnormal arises, and facilitates understanding of overall machine condition for decisions on repairs and repair equipment. The vibration meter detects indicators of the health of the machine workpiece. Vibration in rotating machinery is the back and forth movement or oscillation of a machine and its components, such as grind motors, driven devices (pumps, compressors, and so on), and the bearings, shafts, gears, belts, and other elements that make up the machine workpiece. Excess vibration is symptomatic of internal issues, such as bearing failures, imbalance, misalignment, and looseness that shorten equipment lifespan. Vibration signals detected by the vibration meter can identify issues before other problematic symptoms arise including heat, sound, electrical consumption, and lubricant impurities. Vibration testing via the vibration meter provides a way to determine where the machine workpiece is on a failure curve and react appropriately.

Figure 1B:
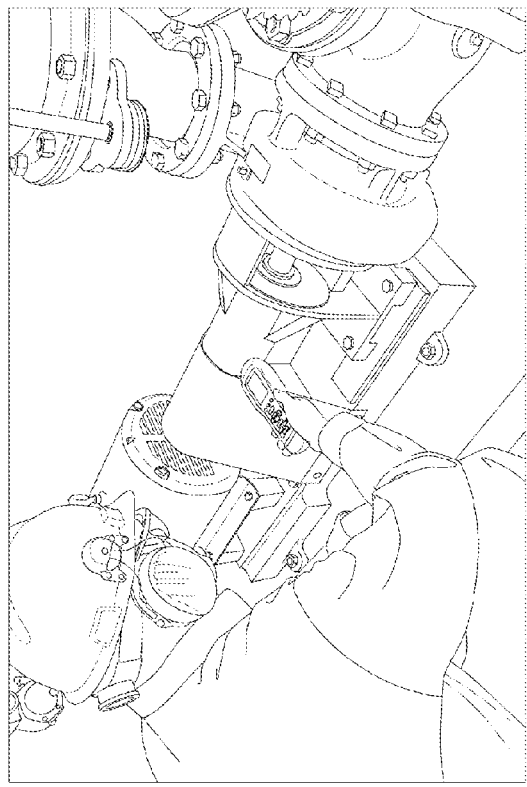
FIG. 1B is a pictorial diagram illustrating a frequency response of a vibration sensor that has not been enhanced.

FIG. 1B illustrates a graph 102 depicting a frequency response of a vibration sensor or an accelerometer that has not been enhanced by various embodiments of the present subject matter. The y-axis represents amplitude in decibels; the x-axis represents frequency in kilohertz. The graph 102 shows the frequency sensitivity of the vibration sensor from 2 kHz onward. Specifically, at 2 kHz, the response is 10 dB; at 6 kHz, the response is about −20 dB; at 15 kHz, the response is about −40 dB; at 23 kHz, the response is about −50 dB; and at 40 kHz, the response is about −55 dB. Such a lack of uniform frequency response is due to many factors in an analog front end or analog domain portion of a circuit, such as piezoelectric crystal dimensions, piezoelectric crystal shape, sensor mechanical packaging, internal filter circuit, mechanical resonance of the piezoelectric crystal, and so on. To detect a vibration signal coming from a vibration sensor and to process it digitally through various pieces of signal processing software so as to provide suitable diagnostic results, the frequency response of the vibration signal suitably should be somewhat uniform throughout a desired frequency band. One such suitable frequency band includes an initial frequency of 4 kHz and a cutoff frequency of 20 kHz. Other suitable frequency bands may be used.

Figure 2:
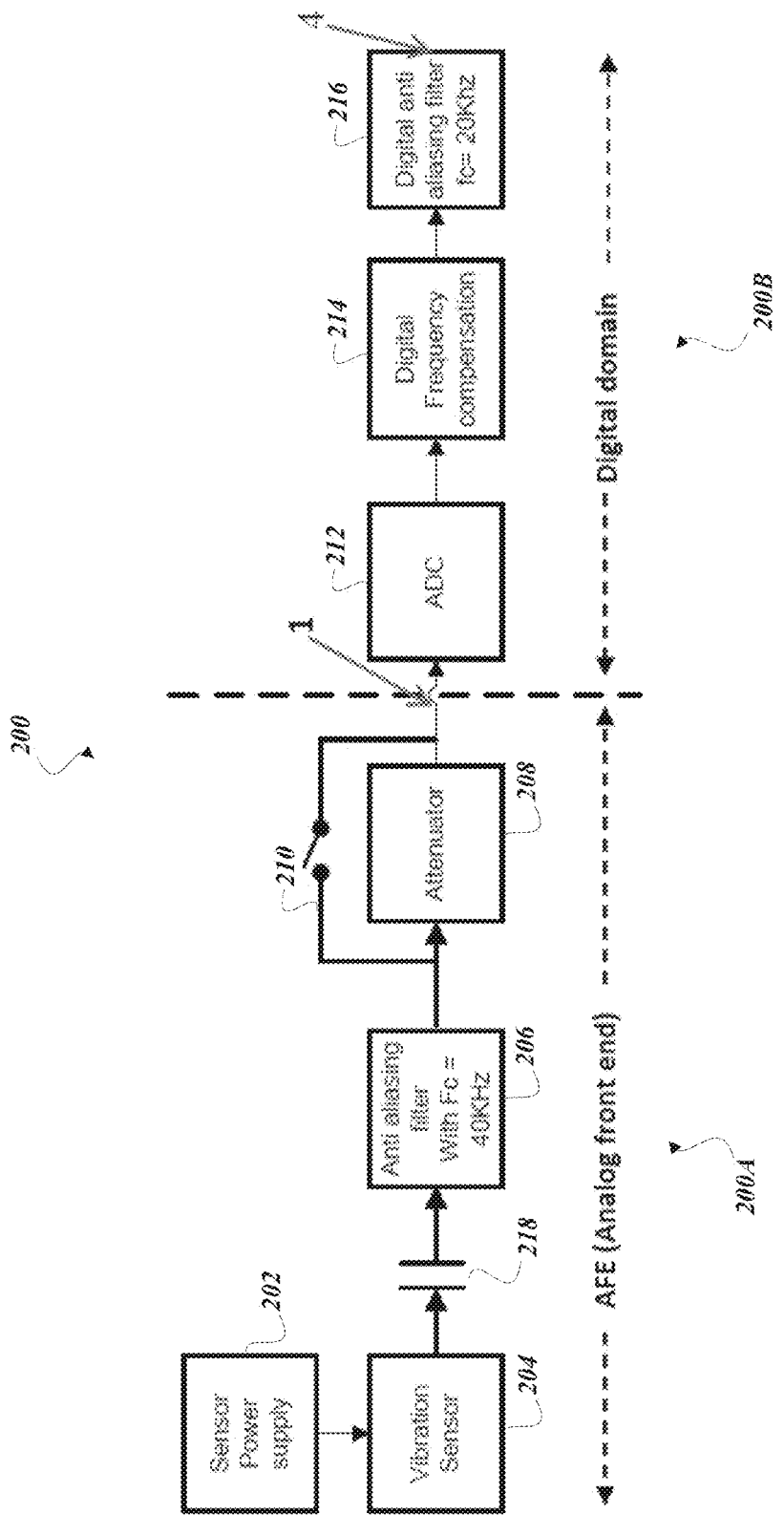
FIG. 2 is a block diagram illustrating an archetypical circuit for enhancing a vibration signal in accordance with various embodiments of the present subject matter.

FIG. 2 illustrates a circuit 200 that enhances a vibration signal so that the frequency response of a vibration sensor from which the vibration signal is generated is somewhat uniform over a desired frequency band, such as between 4 kHz and 20 kHz. In conventional circuits, the desired frequency response is attempted by the use of an analog signal conditioning circuit which causes the noise floor to increase due to amplification provided by the analog signal conditioning circuit. Additionally, conventional circuits require sharp roll-off near the cutoff frequency of a desired frequency band, which cannot be easily achieved economically in an analog circuit. Various embodiments of the present subject avoid or reduce one or more of these problems of conventional circuits. The circuit 200 reduces manufacturing costs by simplifying the design of the analog front end 200a. The circuit 200 in some embodiments improves the signal to noise ratio and/or dynamic range of a vibration meter. In one embodiment, the dynamic range of a vibration meter incorporating the subject matter of various embodiments is about −140 dB and the noise floor is about −120 dB.

Specifically, the circuit 200 is conceptually divided into two sections, an analog front end 200a and a digital domain portion 200b. The analog front end 200a comprises a sensor power supply 202 providing power to a vibration sensor 204. In one embodiment, the vibration sensor 204 includes an accelerometer, which measures acceleration. Either single-axis accelerometers or multi-axis accelerometers may be suitably used. A vibration signal coming from the vibration sensor 204 is presented to a bypass capacitor 218. The bypass capacitor 218 decouples the vibration sensor 204 from the rest of the analog front end 200a by stopping noise and a power signal supplied by the power supply 202 from passing into the analog front end 200a. The bypass capacitor 218 permits high frequency current representative of a portion of interest of the vibration signal to flow to the rest of the analog front end 200a. A bypassed vibration signal is then presented to an anti-aliasing filter with a suitable cutoff frequency. One suitable cutoff frequency includes 40 kHz. The anti-aliased signal is then presented to both a switch 210 and an attenuator 208. The attenuator 208 rescales the anti-aliased signal to the full amplitude scale without appreciably distorting the waveform of the anti-aliased signal to enter the digital domain 200b. The attenuated signal then enters the digital domain 200b from the analog front end 200a to an analog-digital converter 212. The converted signal is then presented to a digital frequency enhancement block 214 on which hardware runs various pieces of signal processing software configured to enhance the frequency response of the converted signal. The enhanced signal is then presented to a digital anti-aliasing filter 216 with a suitable cutoff frequency. One suitable frequency includes 20 kHz.

Figure 3:
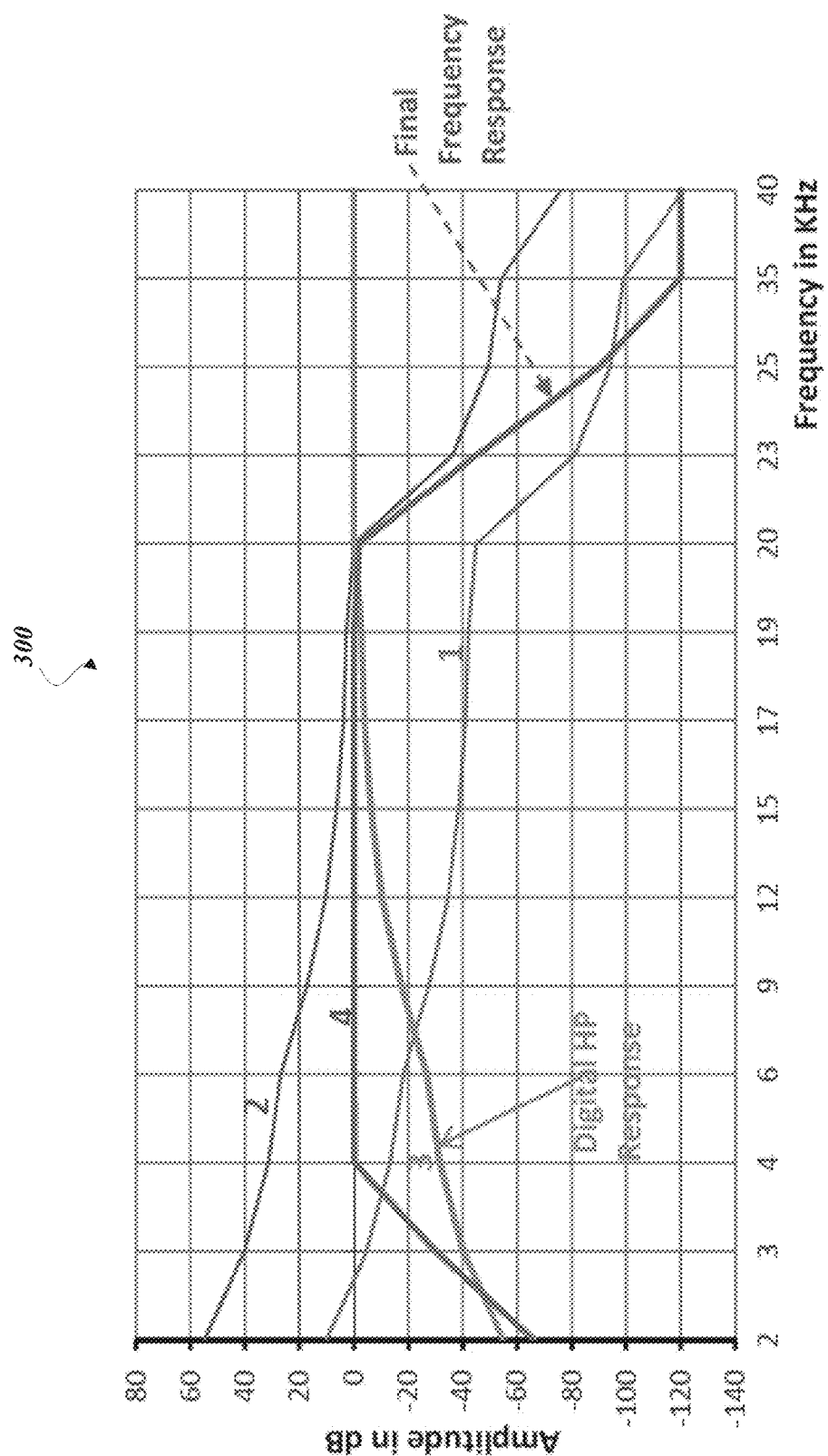
FIG. 3 is a pictorial diagram illustrating archetypical signals that are processed by various embodiments of the present subject matter to enhance frequency response of a vibration sensor.

FIG. 3 illustrates a graph 300 in which various signals are used and generated by pieces of signal processing software in the digital frequency enhancement block 214. The graph is delimited by a y-axis which represents amplitude in decibels and an x-axis which represents frequency in kilohertz. The graph 300 illustrates signal 1, which is the attenuated signal coming from the attenuator 208. Note that the attenuated signal originally derives from the vibration signal coming from the vibration sensor 204. Signal 1's frequency response lacks uniformity over a suitable frequency band, such as 4 kHz to 20 kHz. For example, signal 1's frequency response degrades from about −18 dB at 4 kHz to about −42 at 20 kHz. The digital frequency enhancement block 214 executes pieces of signal processing software to improve the uniformity of the frequency response of signal 1.

The pieces of signal processing software take time domain samples of the attenuated signal and amplify the time domain samples of the attenuated signal using a gain factor to produce a signal 2. The gain factor is calculated from an amplitude of the signal 1 at the cutoff frequency (e.g., 20 kHz). Next, the amplified signal 2 is presented to a digital high-pass filter with a calculated roll-off slope. The calculated roll-off slope of the digital high-pass filter is made based on a suitable amplitude (e.g., −33 dB) of a signal 3 at a suitable initial frequency (e.g., 4 kHz). In one embodiment, the calculated roll-off slope is set to be asymptotic to 0 dB at the cutoff frequency. In another embodiment, the roll-off slope is set to cutoff at a suitable frequency, such as 20 kHz. The filtered signal is presented to the digital anti-aliasing filter with a suitable cutoff frequency. One suitable cutoff frequency includes 20 kHz. Signal 4 is the anti-aliased signal coming out from the digital anti-aliasing filter 216. The signal 4 is then decimated by a digital decimator for further digital signal processing (not shown).

FIGS. 4A-4D illustrate a method 400 for enhancing the frequency response of a vibration signal of a vibration sensor digitally in the time domain. From a start block, the method 400 proceeds to a set of method steps 402 defined between a continuation terminal ("terminal A") and another terminal ("terminal B"). The set of method steps 402 processes an analog signal generated by the vibration sensor. From terminal A (FIG. 4B), the method 400 proceeds to decision block 408 where a test is performed to determine whether the analog front end has received a vibration signal from a vibration sensor. If the answer to the test at decision block 408 is NO, the method proceeds to terminal A and skips back to execute decision block 408 once again. Otherwise, if the answer to the test at decision block 408 is YES, the method 400 proceeds to block 410 where the vibration signal is presented to a bypass capacitor to allow high frequency currents to pass into the analog front end. At block 412, a bypassed vibration signal is presented to an anti-aliasing filter (with suitable cutoff frequency) to rid frequencies that are higher than the Nyquist frequency. At block 414, an anti-aliased signal is presented to an attenuator (or a two-pole filter) to rescale the anti-aliased signal at a desired cutoff frequency in preparation for the digital domain. The method then continues to terminal B.

From terminal B (FIG. 4A), the method proceeds to a set of method steps 404 defined between a continuation terminal ("terminal C") and another terminal ("terminal D"). The set of method steps 404 processes the attenuated signal derived from the analog signal generated by the vibration sensor. From terminal C (FIG. 4C), the method 400 proceeds to decision block 416 where a test is performed to determine whether the attenuated signal is scaled for the digital domain. If the answer is NO to the test at decision block 416, the method continues to terminal C and skips back to decision block 416 where the above-identified processing step is repeated. Otherwise, if the answer to the test at decision block 416 is YES, the method proceeds to block 418 where the method prepares to perform analog-to-digital conversion of the attenuated signal. At block 420, the method quantizes the attenuated signal periodically. The method produces a sequence of digital values that reflect the conversion into a discrete-time and discrete-amplitude signal proportional to the magnitude of the attenuated signal at block 422. The method then continues to terminal D.

From terminal D (FIG. 4A), the method proceeds to a set of method steps 406 defined between a continuation terminal ("terminal E") and another terminal ("terminal F"). The set of method steps 406 executes digital frequency enhancement on the digital signal. From terminal E (FIG. 4D), the method 400 proceeds to decision block 424 where a test is performed to determine whether the converted signal is attenuated at the cutoff frequency. If the answer to the test at decision block 424 is NO, the method continues to terminal C and skips back to decision block 416 where the above-identified processing steps are repeated. Otherwise, if the answer to the test at decision block 424 is YES, the method proceeds to block 426 where the method determines a gain factor based on the amplitude of the attenuated signal at a desired frequency (e.g., 20 kHz). At block 428, the method amplifies the converted signal using acquired time domain samples in the digital domain based on the gain factor. At block 430, the method prepares to digitally enhance the amplified signal so as to obtain somewhat uniform frequency response (of the vibration signal) over a desired frequency band (e.g., 4-20 kHz). At block 432, the method 400 prepares a digital high pass filter. At block 434, the method calculates a roll-off slope of the digital high pass filter. The method then continues to another continuation terminal ("terminal E1").

Figure 4A:
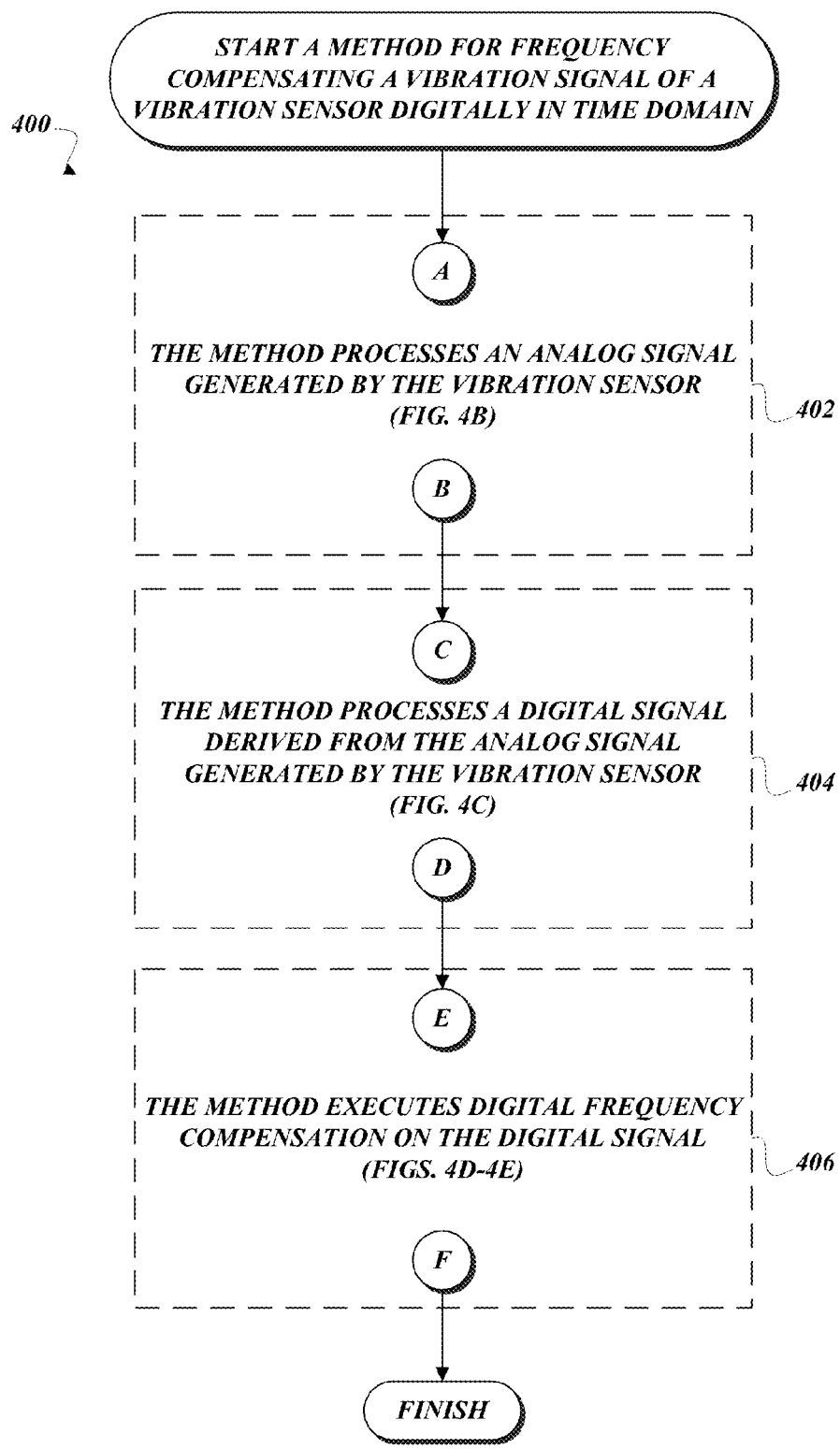
FIGS. 4A-4E are process diagrams illustrating an archetypical method for enhancing frequency response to a vibration signal of a vibration sensor digitally in a time domain.
Figure 4B:
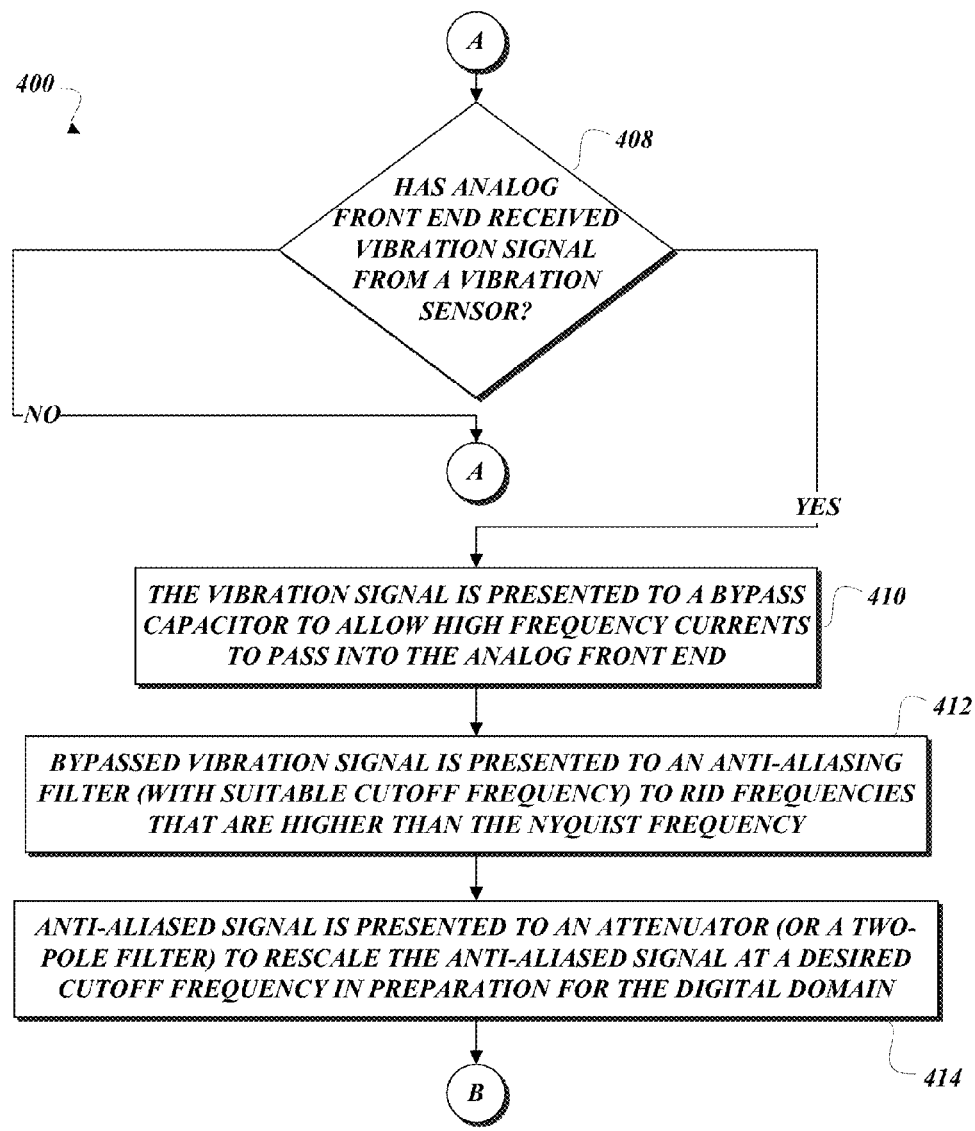
Figure 4C:
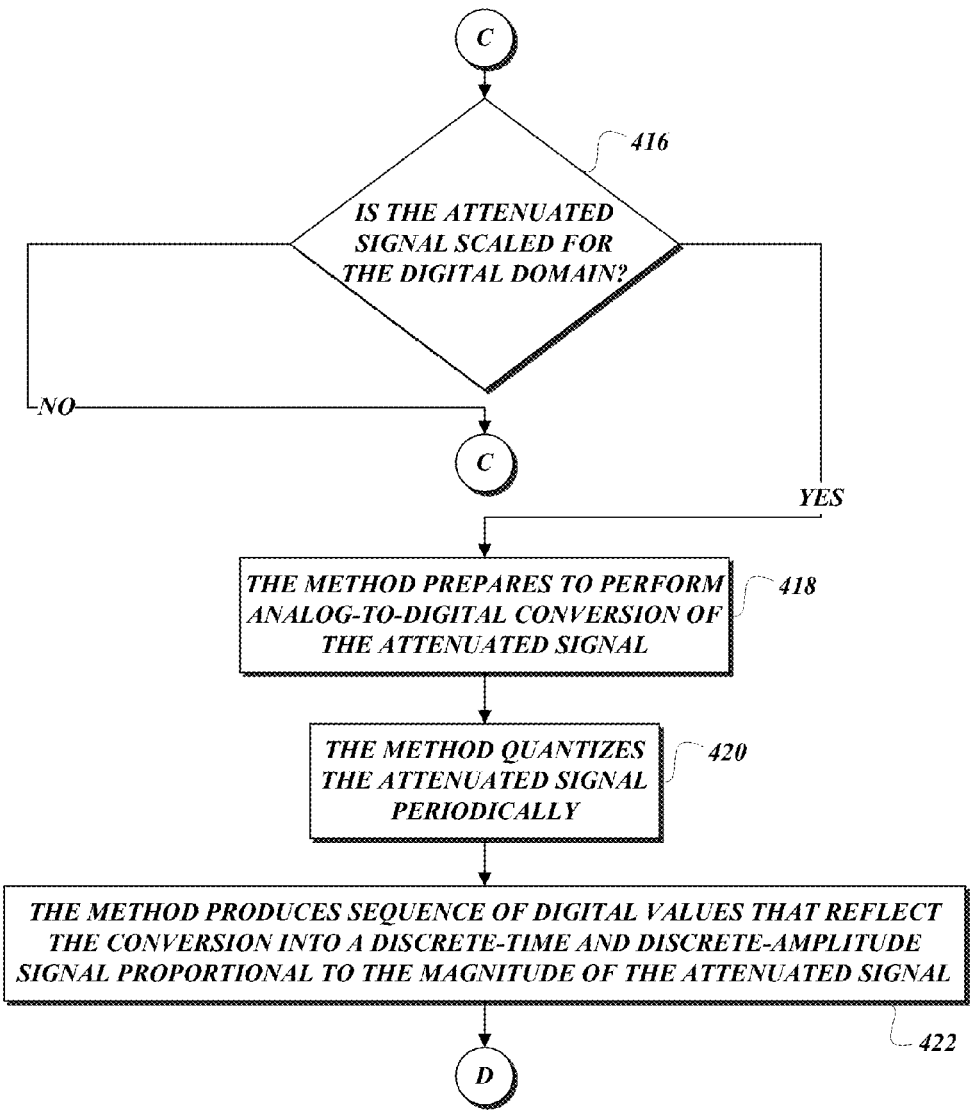
Figure 4D:
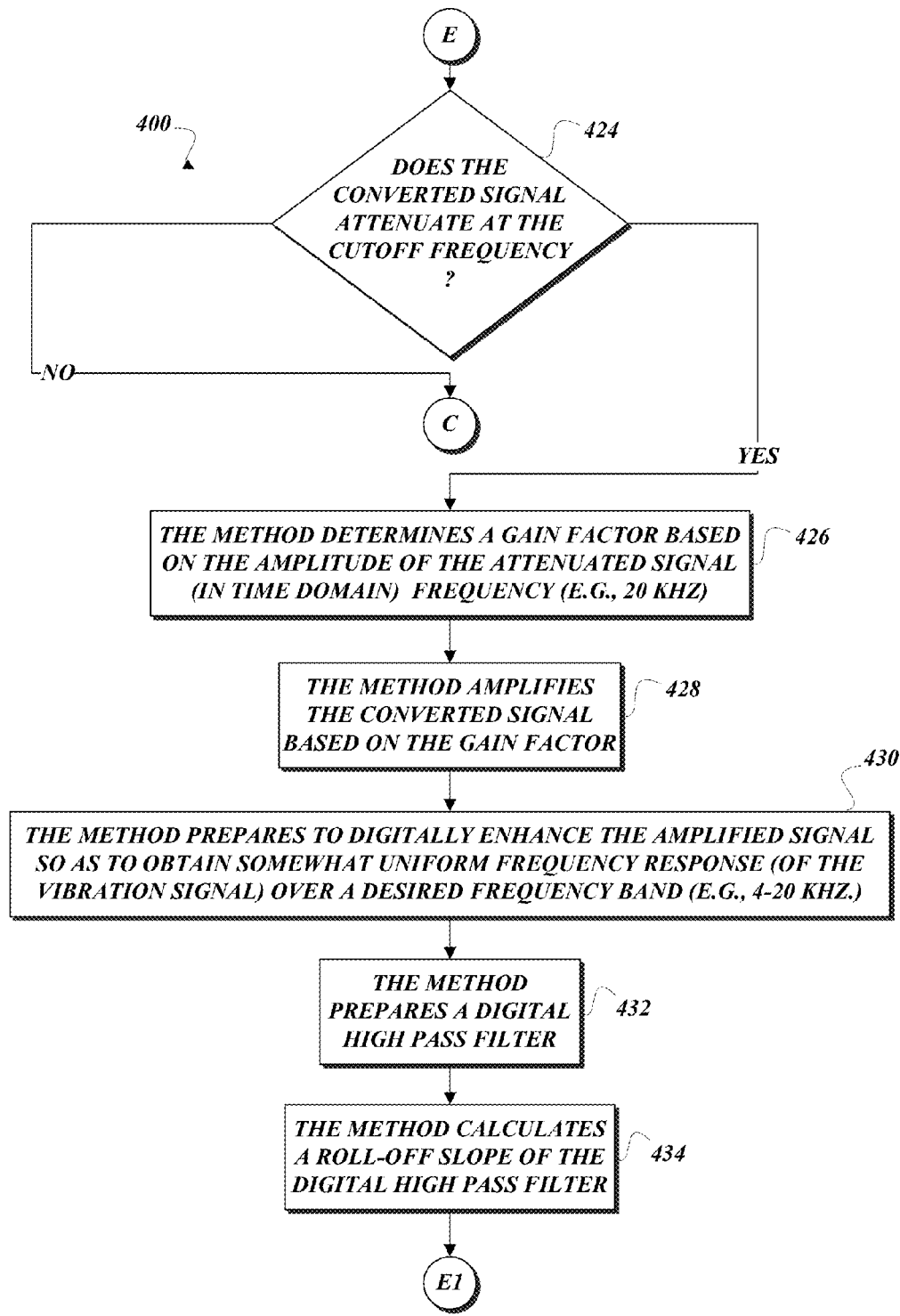
Figure 4E:
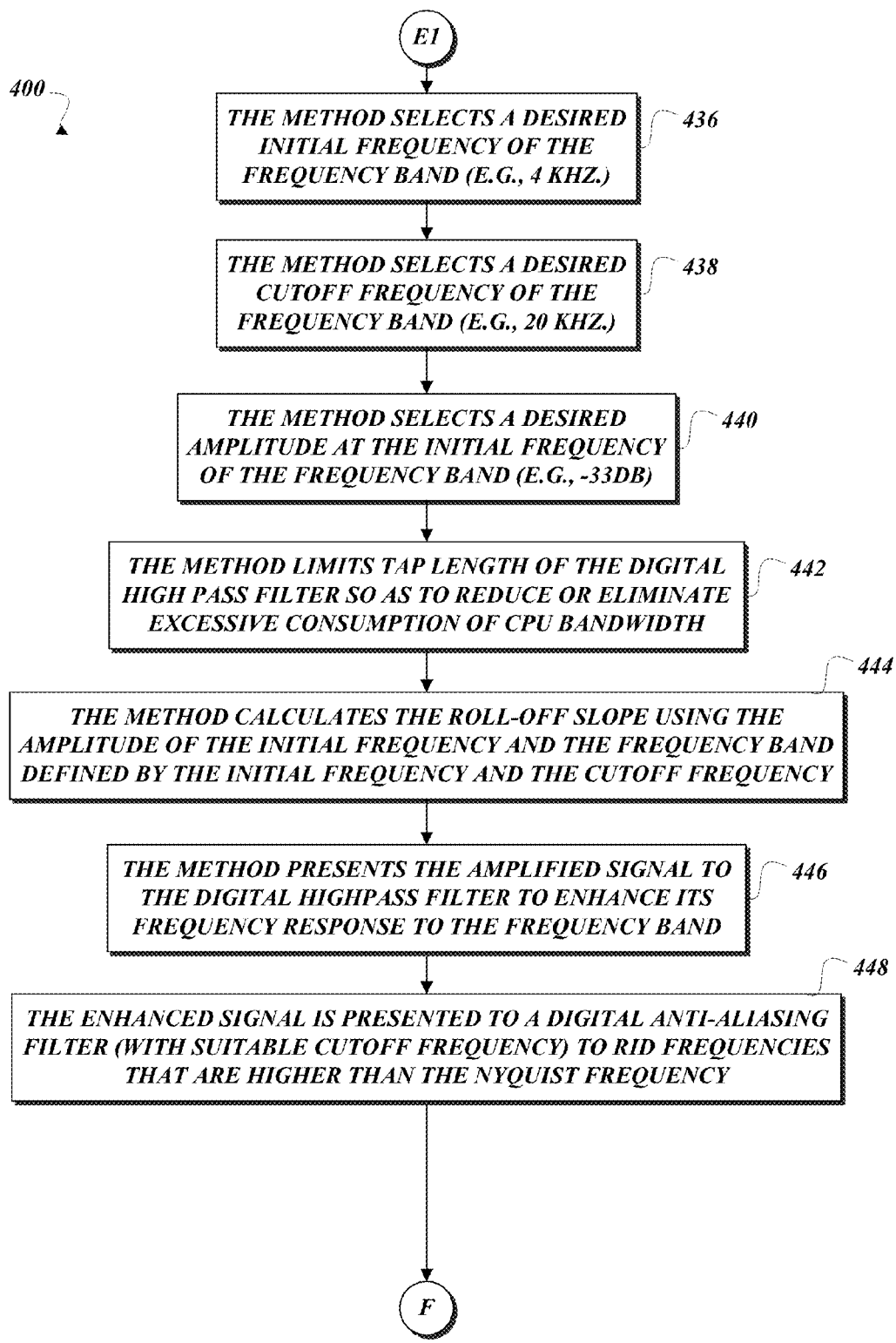

From terminal E1 (FIG. 4E), the method 400 proceeds to block 436 where the method selects a desired initial frequency of the frequency band (e.g., 4 kHz). At block 438, the method selects a desired cutoff frequency of the frequency band (e.g., 20 kHz). At block 440, the method selects a desired amplitude at the initial frequency of the frequency band (e.g., −33 db). At block 442, the method limits tap length of the digital high pass filter so as to reduce or eliminate excessive consumption of CPU bandwidth. At block 444, the method calculates the roll-off slope using the amplitude of the initial frequency and the frequency band defined by the initial frequency and the cutoff frequency. At block 446, the method presents the amplified signal to the digital high pass filter to enhance its frequency response to the frequency band. At block 448, the enhanced signal is presented to a digital anti-aliasing filter (at a suitable cutoff frequency) to purge frequencies that are higher than the Nyquist frequency. The method then continues to terminal F and terminates execution.

While illustrative embodiments have been illustrated and described, it will be appreciated that various changes can be made therein without departing from the spirit and scope of the invention.

The embodiments of the invention in which an exclusive property or privilege is claimed are defined as follows:

1. A vibration meter, comprising:
   an analog-to-digital converter configured to convert an attenuated vibration signal to a converted signal; and
   a digital frequency enhancement block on which hardware runs signal processing software that enhances a frequency response of the vibration meter, wherein the converted signal is amplified by amplifying time domain samples of the attenuated vibration signal to produce an amplified signal, and wherein the amplified signal is filtered to produce a filtered signal by a digital high pass filter having a filter response with a calculated roll-off slope that is based on an amplitude of the filter response at an initial frequency of a frequency band within which the frequency response of the vibration meter is to remain somewhat uniform.

2. The vibration meter of claim 1, further comprising a digital anti-aliasing filter having a cutoff frequency of about 20 kHz, wherein the filtered signal is presented to the digital anti-aliasing filter to produce an anti-aliased signal.

3. The vibration meter of claim 1, further comprising a sensor power supply.

4. The vibration meter of claim 3, further comprising a vibration sensor coupled to the sensor power supply to receive power, wherein the vibration sensor senses vibrations and produces a vibration signal.

5. The vibration meter of claim 4, further comprising a bypass capacitor coupled to the vibration sensor to receive the vibration signal and to produce a bypassed signal.

6. The vibration meter of claim 5, further comprising an analog anti-aliasing filter having a cutoff frequency of about 40 kHz, wherein the bypassed signal is presented to the analog anti-aliasing filter to produce an anti-aliased signal.

7. The vibration meter of claim 6, further comprising an attenuator, wherein the anti-aliased signal is presented to the attenuator to produce the attenuated vibration signal.

8. A method for a vibration meter, the method comprising:
   converting, by an analog-to-digital converter, an attenuated vibration signal to a converted signal; and
   digitally enhancing a frequency response of the vibration meter by a digital frequency enhancement block, wherein said digitally enhancing the frequency response includes amplifying the converted signal by amplifying time domain samples of the attenuated vibration signal to produce an amplified signal, and filtering the amplified signal by a digital high pass filter to produce a filtered signal, wherein the digital high pass filter has a filter response with a calculated roll-off slope that is based on an amplitude of the filter response at an initial frequency of a frequency band within which the frequency response of the vibration meter is to remain somewhat uniform.

9. The method of claim 8, wherein the converted signal is amplified by amplifying the time domain samples of the attenuated vibration signal using a gain factor, wherein the gain factor is calculated from an amplitude of the attenuated vibration signal at a cutoff frequency of the frequency band.

10. The method of claim 9, wherein the calculated roll-off slope is set to be asymptotic to 0 dB at the cutoff frequency.

11. The method of claim 8, further comprising digitally anti-aliasing the filtered signal by a digital anti-aliasing filter to produce a digital anti-aliased signal.

12. The method of claim 8, further providing power by a sensor power supply.

13. The method of claim 12, further comprising receiving a vibration signal by a vibration sensor coupled to the sensor power supply to receive power.

14. The method of claim 13, further comprising de-coupling the vibration signal by a bypass capacitor coupled to the vibration sensor to produce a bypassed signal.

15. The method of claim 14, further comprising anti-aliasing the bypassed signal by an analog anti-aliasing filter to produce an analog anti-aliased signal.

16. The method of claim 15, further comprising attenuating the analog anti-aliased signal by an attenuator to produce the attenuated vibration signal.

17. A tangible computer-readable medium on which computer-executable instructions are stored that, in response to execution, cause a vibration meter to:

convert, by an analog-to-digital converter, an attenuated vibration signal to a converted signal; and digitally enhance a frequency response of the vibration meter by a digital frequency enhancement block, wherein:

the converted signal is amplified by amplifying time domain samples of the attenuated vibration signal to produce an amplified signal, and the amplified signal is filtered to produce a filtered signal by a digital high pass filter having a filter response with a calculated roll-off slope that is based on an amplitude of the filter response at an initial frequency of a frequency band within which the frequency response of the vibration meter is to remain somewhat uniform.

18. The computer-readable medium of claim 17, wherein the converted signal is amplified by amplifying the time domain samples of the attenuated vibration signal using a gain factor, wherein the gain factor is calculated from an amplitude of the attenuated vibration signal at a cutoff frequency of the frequency band.

19. The computer-readable medium of claim 18, wherein the calculated roll-off slope is set to be asymptotic to 0 dB at the cutoff frequency.

20. The computer-readable medium of claim 19, wherein the instructions, in response to execution, further cause the vibration meter to digitally anti-alias the filtered signal by a digital anti-aliasing filter to produce a digital anti-aliased signal.

* * * * *